United States Patent
Ueckert

(10) Patent No.: US 10,238,477 B1
(45) Date of Patent: Mar. 26, 2019

(54) SYSTEMS AND METHODS FOR DETERMINING AND MAINTAINING AN ORTHOPEDICALLY OPTIMIZED CRANIO-CERVICAL/CRANIO-MANDIBULAR POSITION

(71) Applicant: Gregg Edward Ueckert, Austin, TX (US)

(72) Inventor: Gregg Edward Ueckert, Austin, TX (US)

(73) Assignee: Gregg Edward Ueckert, Austin, TX (US)

( * ) Notice: Subject to any disclaimer, the term of this patent is extended or adjusted under 35 U.S.C. 154(b) by 0 days.

(21) Appl. No.: 15/443,882

(22) Filed: Feb. 27, 2017

Related U.S. Application Data

(60) Provisional application No. 62/439,350, filed on Dec. 27, 2016.

(51) Int. Cl.
| | |
|---|---|
| *A61N 1/00* | (2006.01) |
| *A61C 19/05* | (2006.01) |
| *A61N 1/04* | (2006.01) |
| *A61N 1/36* | (2006.01) |
| *A63B 71/08* | (2006.01) |

(52) U.S. Cl.
CPC .......... *A61C 19/05* (2013.01); *A61N 1/0456* (2013.01); *A61N 1/36014* (2013.01); *A63B 71/085* (2013.01)

(58) Field of Classification Search
CPC .... A61C 19/05; A61C 7/08; A61H 2205/026; A61N 1/18; A61N 1/0456; A61N 1/36; A61N 1/36014; A61B 71/085
See application file for complete search history.

(56) References Cited

U.S. PATENT DOCUMENTS

| | | | |
|---|---|---|---|
| 8,667,972 B2 | 3/2014 | Makkar | |
| 2011/0209714 A1* | 9/2011 | Makkar | ............... A63B 71/085 128/861 |
| 2014/0093834 A1* | 4/2014 | Andary | .................. A61F 5/566 433/6 |

\* cited by examiner

*Primary Examiner* — Scott M. Getzow
(74) *Attorney, Agent, or Firm* — Sprinkle IP Law Group

(57) ABSTRACT

Systems and methods for systems and methods for improvement of a person's performance and well-being by determining and maintaining an orthopedically optimized position of the person's jaw. In one embodiment, TENS is applied to the patient's jaw muscles to relax and deprogram the muscles, the person's TMJs are evaluated and reduced, and neural shear in the patient's upper cervical spine is minimized by orthopedically aligning the patient's head and neck (CC complex), thereby causing the patient's jaw to move toward an orthopedically optimized position (CM complex). A bite registration of the upper and lower jaws is taken, with molars and premolars at least 2 millimeters apart, the front teeth not touching, and preferably a vertical index of 17-21 millimeters. Molds of the persons upper and lower teeth may be positioned using the bite registration, and an orthopedic alignment device (OAD) may be formed between the molds.

18 Claims, 6 Drawing Sheets

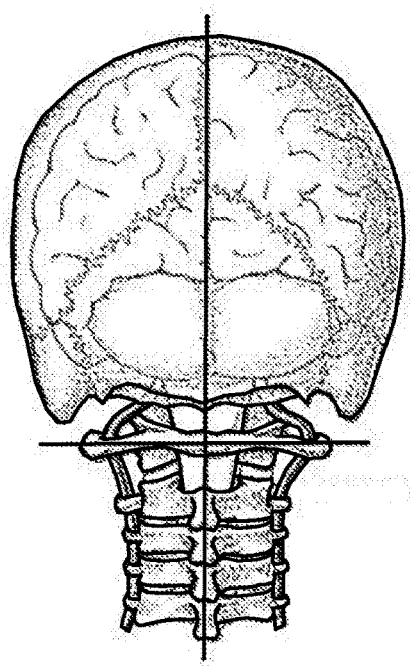 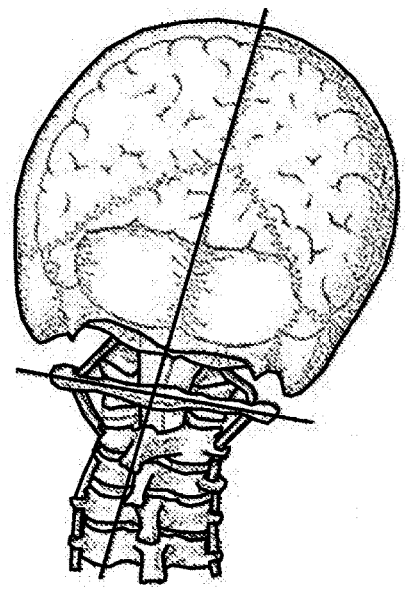
Fig. 7A  Fig. 7B
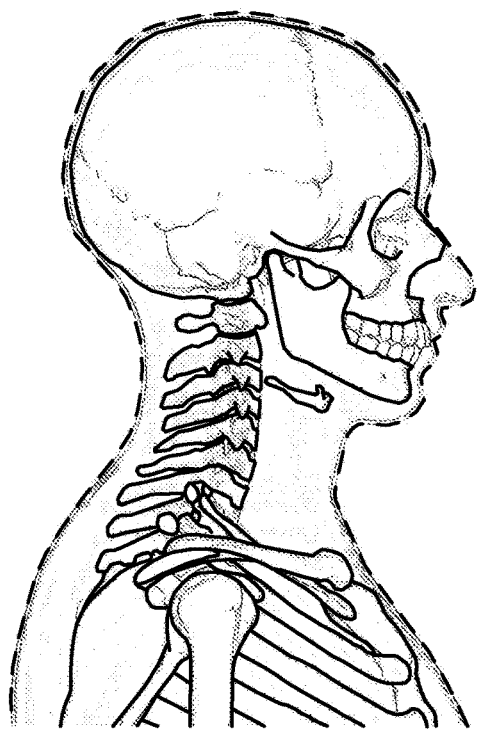 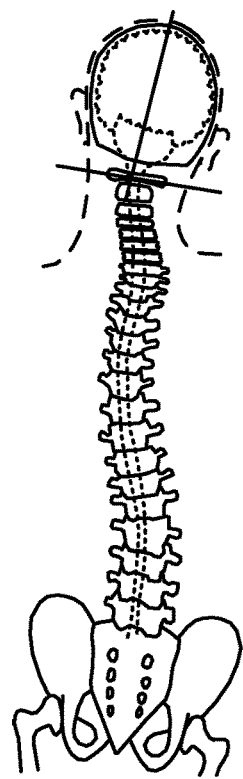
Fig. 8  Fig. 9

SYSTEMS AND METHODS FOR DETERMINING AND MAINTAINING AN ORTHOPEDICALLY OPTIMIZED CRANIO-CERVICAL/CRANIO-MANDIBULAR POSITION

CROSS-REFERENCE TO RELATED APPLICATIONS

This application claims the benefit of U.S. Provisional Patent Application 62/439,350, filed Dec. 27, 2016 by Gregg Ueckert, which is incorporated by reference as if set forth herein in its entirety.

BACKGROUND

Field of the Invention

The invention relates to manufacturing and using orthopedic alignment devices that are designed to maintain an optimized orthopedic alignment of the upper and lower jaws and thereby promote optimized orthopedic alignment of the head and upper cervical spine.

Related Art

Protective mouthpieces have long been used by athletes, ostensibly for the purpose of avoiding damage to their teeth. These mouthpieces may also be intended to reduce the effects of concussive impacts to the jaw. More recently, it has been discovered that mouthpieces may, by maintaining a desired position of the lower jaw with respect to the upper jaw, affect an athlete's performance and well-being. In addition, poor head position induces torque in the upper cervical spine, creating shear on the central nervous system (CNS) and limiting range of motion in the major joints of the body. This prevents optimal physiologic output and presents an increasing risk of injury through accommodation to the restricted movements and less than optimal physiologic alignment. It would therefore be desirable to be able to determine an optimized position of an athlete's (or other person's) lower jaw with respect to his upper jaw (or cranium) and an optimized position of the upper cervical spine relative to the cranium. Maintaining this optimized Cranio-Cervical/Cranio-Mandibular (CC/CM) position increases and preferably maximizes physiologic performance, while reducing and preferably minimizing risk of injury by correcting misalignment in the postural chain and restoring proper range of motion to affected joints. This can eliminate chronic pain or injuries in athletes that are otherwise unresolved.

SUMMARY OF THE INVENTION

This disclosure is directed to systems and methods for systems and methods relating to the improvement of a person's orthopedic alignment, from the head, descending down the postural chain to the feet. This can maximize physiologic performance and eliminate or minimize injuries that are directly related to poor head position which causes poor alignment of the postural chain. The improvement is achieved through the optimization of the CC/CM relationship.

One exemplary embodiment comprises a method in which CC/CM alignment is an orthopedically optimized and the corresponding position of a patient's jaw and upper cervical spine (vertebrae C1 and C2) is determined. In this embodiment, the patient's temporo-mandibular joints (TMJs) are first evaluated for Articular Disc Displacement (ADD) and orthopedic alignment while closing on their back teeth. If ADD is detected, then disc reduction is necessary to ensure that the articular disk of each TMJ is properly positioned between a condyle of the patient's lower jaw and the corresponding glenoid fossa of the patient's cranium. Ultra Low Frequency TENS (e.g., 0.76 Hz) is applied to stimulate cranial nerve V (the trigeminal nerve), which deprograms and relaxes the muscles that support the patient's lower jaw and the mandible to identify physiologic rest of the mandible and aid in decompression of the TMJs and disc reduction in cases where ADD is present (CM component). Additionally, during optimization of the position of the TMJs and the lower jaw, neural shear in the central nervous system (brain stem) is relieved by optimizing the alignment of the patient's upper cervical spine relative to the cranium (CC component). In the optimization process, this includes, for example, ensuring that the patient's bipupillary line and ala-tragus line are level with horizon, as well as ensuring that any forward head posturing is corrected by verifying that the patient's ears are directly above the patient's shoulders, hips, knees and heels.

Applying TENS and orthopedically aligning the patient's CC complex will cause the patient's jaw to move toward a more ideal, orthopedically optimized CM position than it would otherwise obtain without CC correction. To obtain this advanced CC/CM optimized jaw relationship and to reduce ADD if present, alignment of C1 and C2 (CC alignment) is performed first. Then, the patient's lower jaw position (CM alignment) is optimized by protruding the lower jaw forward while TENS is applied. This is actually performed in several (e.g., five to seven) cycles. In each cycle, the lower jaw is protruded forward to a protrusive, anteriorly extended position for a short period of time (e.g., five to seven TENS pulses) and then allowed to float and relax to the more desirable orthopedically optimized position. These cycles are performed concurrently with maintaining upper cervical alignment of C1 and C2 (CC/CM alignment).

While the neural shear in the patient's upper cervical spine is relieved by distraction of C1 and C2 (CC alignment) and the lower CM relationship has been optimized (and after the TMJs' ADD has been reduced, if necessary) a bite registration of the upper and lower jaws is taken to lock CM alignment, thereby holding CC alignment. This six-dimensional point in space in which the bite registration is taken will generally have the patient's upper and lower molars and premolars about 2-4 millimeters apart, and with the patient's lower and upper front teeth not touching each other. A "Golden", or ideal, vertical dimension of 17-21 mm is desirable in the final bite registration, with the reference point being the Cemento-Enamel Junction (CEJ) of the two most directly opposed maxillary and mandibular incisors when the patient is closed into the optimized bite registration.

In one embodiment, the method also includes providing impressions or digital scans to fabricate models of the patient's upper and lower teeth. The models are then mounted relative to one another on an articulator. The models are mounted in the orthopedically optimized CC/CM position using the bite registration. An orthopedic alignment device (OAD) is formed between the models to hold the CC/CM alignment which was achieved during the fitting. The OAD is formed so that when the OAD is positioned in the patient's mouth and the patient's jaw is closed, bite pressure is applied to the patient's upper molars and premolars and lower molars and premolars, placing the CC/CM complex into its orthopedically aligned position established during the fitting process. This CC/CM position decompresses the TMJs, reduces ADD in the TMJs in the orthopedically optimized CM position, thereby causing the head and neck to move to the orthopedically optimized CC position. The OAD preferably applies bite pressure to the patient's upper and lower molars and premolars, and no bite pressure is applied to the anterior teeth.

Numerous other embodiments are also possible.

BRIEF DESCRIPTION OF THE DRAWINGS

Other objects and advantages of the invention may become apparent upon reading the following detailed description and upon reference to the accompanying drawings.

FIGS. 7A and 7B are diagrams illustrating exemplary posterior views of the cervical spine in an aligned position and a non-aligned position, respectively.

FIG. 8 is a diagram illustrating an exemplary lateral view of the cervical spine in an aligned position.

FIG. 9 is a diagram illustrating an exemplary posterior view of the full spine in a non-aligned position.

Figure 1:
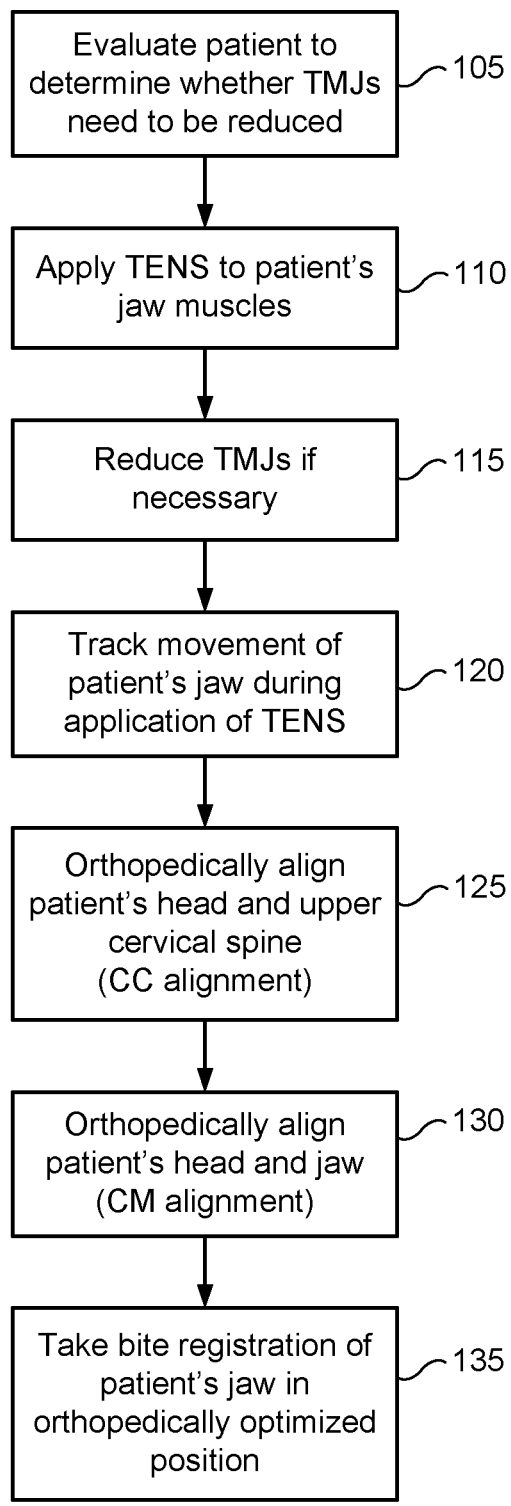
FIG. 1 is a flow diagram illustrating a method for making a bite registration for an orthopedically optimized CC/CM position in accordance with one embodiment.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

One or more embodiments of the invention are described below. It should be noted that these and any other embodiments described below are exemplary and are intended to be illustrative of the invention rather than limiting.

As described herein, various embodiments of the invention comprise systems and methods for promoting optimized orthopedic alignment of the head and upper cervical spine through the use of OAD's that maintain CC alignment via an optimized CM orthopedic alignment of the TMJs and upper and lower jaws As noted above, the position of a person's jaw may affect his or her well-being and performance. Various studies have been conducted in relation to the effect of jaw position on performance. For example, U.S. Pat. No. 8,667,972 to Makkar, et al. (which is incorporated herein by reference) briefly notes several articles on the use of mouthpieces to maintain a physiological resting position of the jaw and thereby enhance physical performance. While these studies and the remainder of Makkar's disclosure discuss the positioning of the lower jaw with respect to the skull, they do not take into account alignment of the skull with the spine (CC alignment) and its affect on the positioning of the mandible with respect to the skull (CM positioning). In the absence of proper CC alignment, the jaw position that is determined through the prior art methodologies does not optimize the jaw position, so the person's maximum performance and minimized risk of injury is not obtained through these methodologies. The shortcoming of these methodologies is that they fail to ensure that neural shear (which is used herein to refer to the stress on the spinal cord at the skull and upper cervical vertebrae) has been minimized or relieved, so they fail to restore proper function to major joints' ranges of motion.

Before describing exemplary embodiments of the invention, it may be helpful to explain some aspects of the relationship between CC alignment, CM alignment and their impact on performance and minimizing risk of injury. The spinal cord emerges from the skull through the foramen magnum—the large opening at the base of the skull—and extends through the vertebrae, including the uppermost cervical vertebra (referred to as C1, or the "atlas") and the second cervical vertebra (referred to as C2, or the "axis"). The atlas and axis enable 70% of the movement of the skull with respect to the spine. When the skull and cervical vertebrae are perfectly aligned, as will be described in more detail below (see FIGS. 7A and 8), neural shear on the spinal cord within the atlas and axis is minimized. Whenever the skull moves away from this concentrically aligned position, the spinal cord is moved with it, which places torque on the central nervous system. This torque is induced by a direct physical connection of the atlas and axis via a connective tissue bridge to the dura mater, which is a thick membrane that is the outermost of the three layers of the meninges that surround the brain and the spinal cord. The dura mater functions as a sort of "skin" that covers and protects the brain and central nervous system. When the dura mater is stretched or twisted by movement of the head or neck away from optimal alignment, torque is induced into the central nervous system. If the shear stress on the spinal cord is too high, range of motion is immediately limited to prevent further shear of the central nervous system and nerve tissue. Pain emanating from nociceptors can also signal the brain to limit the body's range of motion. This pain sensation inhibits further movement and corresponding stress on the spinal cord. For example, if person's head is side bent and turned to the left, shear forces will be placed on the brachial plexus of nerves that innervate the right arm. The range of motion of the right shoulder will be limited to prevent further shear from occurring, and the induced compression and misalignment of the nerves can cause paraesthesia in the affected arm into the hand. This misalignment can descend down the postural chain, affecting alignment down to the feet. In addition to creating shear forces or compression on the person's nerves and consequent pain, the misalignment can cause constriction of the vertebral artery (see FIG. 7B), potentially resulting in problems such as vascular migraine headaches, and high blood pressure as the heart pumps harder to adequately perfuse blood into the brain.

In the prior art, a physiological resting position of the jaw may be determined by applying TENS (transcutaneous electric neural stimulation) to a patient's jaw muscles to relax these muscles. When the physiological resting position has been determined, a bite registration can be recorded and used to manufacture a mouthpiece for the patient. When worn by the patient, the mouthpiece will keep the patient's lower jaw in a position that is aligned with the physiological resting position. By maintaining this position, the patient's performance will be enhanced in comparison to his or her performance when the jaw is in a typical position in which the lower jaw is posterior to the physiological resting position.

In the present methods, TENS is applied to the patient's jaw muscles to relax the muscles. This may also be referred to as "deprogramming" the jaw muscles, because the patient has created an engram pattern of muscle contraction to lift the lower jaw and couple the posterior teeth into a position posterior to the physiological resting position. Before the physiological resting position is determined, the neural shear on the patient's brain stem is minimized by positioning the CC alignment of the patient's head via cervical distraction to align the upper cervical spine (C1 and C2), thereby leveling the head in both the frontal and lateral views and removing forward head posturing to balance head position. The movement of the head to this position will directly affect the resting position of the lower jaw with respect to the upper jaw. For example, if the head is forward-positioned and posterior-cranial-rotated, correcting this will directly affect the resting position of the jaw, moving it forward. With the head in an orthopedically aligned position and the jaw muscles deprogrammed, the jaw will be in an orthopedically optimized, more anterior position of rest. When the CC/CM position is at the orthopedically optimized position, a bite registration is recorded. This bite registration is used to manufacture an OAD for the patient. When the patient uses the OAD, the patient's CC/CM complex will be maintained in the orthopedically optimized position when the mandible is closed into the OAD, and this will cause the patient's head to move to the orthopedically optimized position. This will in turn reduce neural shear and enable increased performance, and will minimize risk of repetitive injury.

Referring to FIG. 1, a flow diagram illustrating a method in accordance with an exemplary embodiment is shown. In this embodiment, the orthopedically optimized position of a patient's jaw (see FIG. 3) is determined, and is used to manufacture an OAD that maintains the orthopedically optimized position when worn by the patient. By maintaining the orthopedically optimized jaw position, particularly when proprioception of jaw position occurs, orthopedic alignment of the head and upper cervical spine is maintained, neural shear is reduced, range of motion in the major joints is improved, and balance is improved. This reset of orthopedic alignment also minimizes risk of injury.

The jaw joint is the most unique and most used joint in the body. This joint functions as a rotational joint in the first 20 mm of opening, and in the last 20-25 mm of opening translation of the joint occurs. During this translation, the condyle of the mandible moves out of the glenoid fossa to reach maximum opening. The lower jaw can move in six translational directions—up/down, forward/backward, and side-to-side. In addition to this, it can also move in the same rotational directions as an airplane, referred to as pitch, yaw and roll. For example, if person closes his jaw and the front teeth touch before the back teeth, the lower jaw will pitch up in back until the back teeth touch. If the front left teeth touch on one side first before the other side, the jaw will yaw away from the premature contact to avoid the interference. And if the back teeth on the right side touch before the back teeth on the left side touch the jaw will roll up on the left side until the posterior teeth touch. When the lower jaw has to pitch yaw or roll, it creates compression in the TMJs, which results in torque in the upper cervical spine (C1 and C2), immediately developing neural shear. To manage this shear, the jaw has to be balanced in all 6 directions. This is accomplished using the OAD.

The concept of interaction or interdependence of the CM alignment and the CC alignment is sometimes referred as the 50-50 principle, pioneered by Dr. Mariano Rocabodo. The commonality between the relationships is the skull, and changing one of the alignments affects the other—the Action/Reaction Law. If the alignment of the lower jaw and upper jaw is improved, the alignment of the cervical spine also improves. Conversely, if the alignment of the cervical spine is improved, the alignment of the upper and lower jaws will improve.

Figure 2:
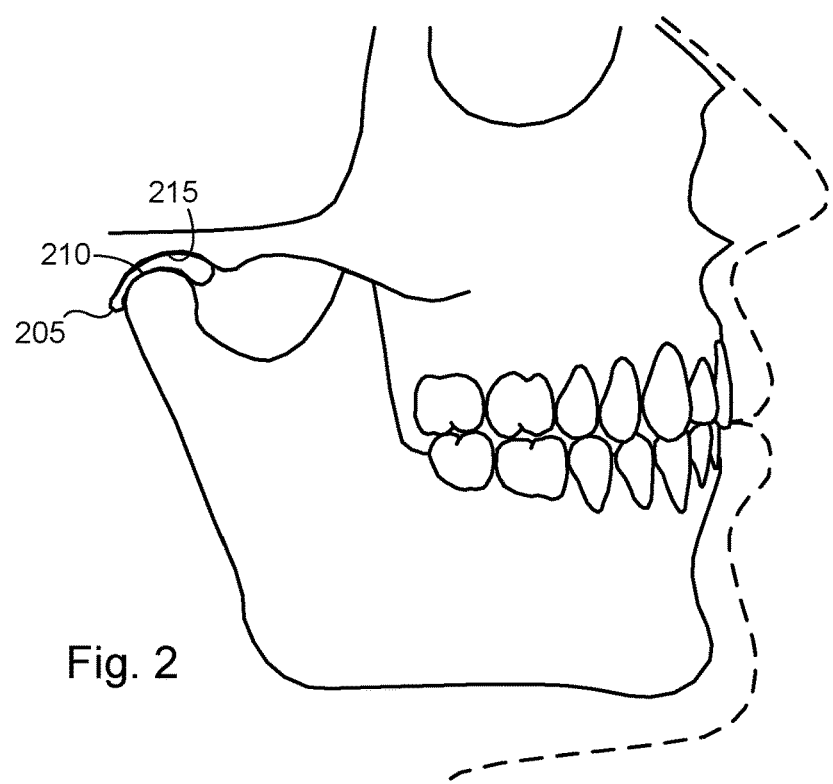
FIG. 2 is a diagram illustrating a patient's jaw in a position that is not orthopedically optimized, and has ADD in the TMJ.

In a normally (but not optimally) aligned CC/CM relationship, when a person's jaw closes, the upper front teeth are positioned in front of (anterior to) the lower front teeth (see FIG. 2). The posterior teeth on the Right and Left contact at the same time without generating any pitch/yaw/roll before the anterior teeth touch. The right and left TMJ articular discs are stable and reduced without any anterior displacement in the glenoid fossa, and C1 and C2 are concentrically aligned without any subluxation or rotation. In a subluxated alignment, the lower jaw must move up and back to seat the posterior teeth. This compresses the TMJs, leading to ADD and causing subluxation of C1/C2, forward head posturing with possible rotation and side bending, and cascading misalignment down the postural chain. This up-and-backward movement of the jaw also causes occlusion of the person's airway by limiting tongue space. Additionally, the person's tongue moves backward to avoid being bitten, which further occludes the airway, leading to obstruction while sleeping and increasing the incidence of snoring or obstructive sleep apnea. In response to the occlusion of the airway and the collapse of the jaw relationship due to loss of posterior bite support, descending subluxation of the postural chain occurs as the person's head moves forward. This is dictated by the action/reaction law, creating obstructions in joint movement (like Femoral-Acetabular-Impingement or FAI) and helping maintain a more open airway. This forward movement of the head in turn affects the central nervous system by placing torque on the brain stem, generating neural shear in the upper cervical spine, and causing the atlas and axis to subluxate, which also limits the range of motion in the major joints.

Proprioception is the sense of the relative position of neighboring parts and strength of effort being employed in movement of the body parts. This term is therefore used to describe the sensory information that contributes to the sense of position and movement of the jaw. The receptors from our muscles and joints innately inform us and give us body awareness and provide information on how we are moving.

The proprioceptive system is located primarily in the cerebellum (the balance center of the brain) and it works closely with the vestibular system and tactile system. The spinocerebellum regulates tone, posture and equilibrium by receiving sensory impulses from proprioceptors, tactile receptors, visual receptors and auditory receptors. In the case of the jaw, it is the trigeminocerebellar tract that provides the proprioceptive efferent connection to the spinocerebellum. This tract conveys proprioceptive information from the jaw muscles and the TMJs to the spinocerebellum. It also carries the sensory impulses from the periodontal tissue (the ligaments and tissue that supports the teeth in the jaw bone) to the spinocerebellum.

The proprioception of the relationship of the jaw, TMJs and teeth is provided directly to the cerebellum. When the posterior teeth (molars and premolars) make contact, proprioception via the trigeminocerebellar tract communicates with the spinocerebellum instantly, using the information to effect head position. This occurs, on average, about 3000 times each day. Consequently, if a person's jaw is out of alignment, the position of the person's head will also be out of alignment.

The CC/CM alignment of a patient can be corrected so that his or her head position is not subluxated, but is instead orthopedically optimized. More specifically, it can be held in an optimized orthopedically aligned position in which neural shear is relieved and the head is back at its optimized balance point, initiating a descending cascade of realignment down the postural chain. This results in improved range of motion of major joints, improved balance, more patent airway, maximized motor recruitment and minimized risk of injury. The improvement is immediate and can be assessed using normal range-of-motion tests for the upper cervical spine, lower cervical spine, shoulders and hips. In the case of patients who have pain that derives from subluxation of the CC/CM complex, optimization of this complex reduces neural shear and immediately decreases pain in joints that were limited in range of motion.

Figure 3:
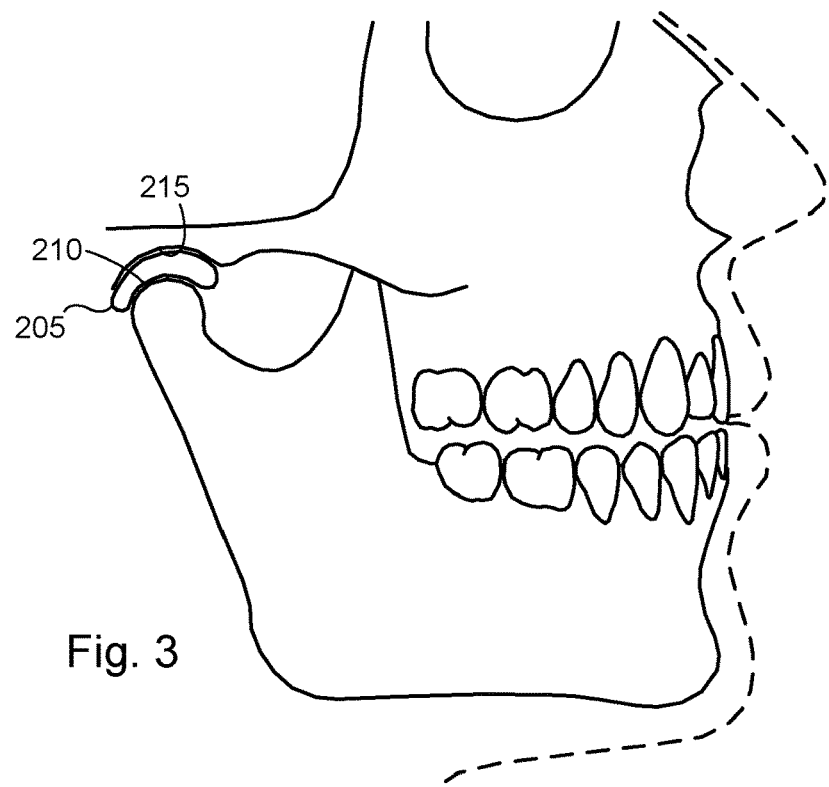
FIG. 3 is a diagram illustrating a patient's jaw at its orthopedically optimized CM relationship in a position that has decompressed the condyle in the glenoid fossa and reducing the disc in the TMJ.

In the method of FIG. 1, the patient is first evaluated to determine whether there is any ADD in the TMJs (105). As shown in FIGS. 2 and 3, an articular disk 205 is positioned between the condyle 210 of the lower jaw and the glenoid fossa 215 of the temporal bone. Normally, as the jaw is opened and closed, the disks move so that they remain between the condyle and the fossa. In some cases, as the jaw is closing and the posterior teeth are coming into terminal contact, the condyle moves up and back, compressing the TMJ and placing load on the posterior portion of the articular disc. This causes ADD, generating a pop or click of the TMJ upon closing. As the jaw is opened, the disc can be reduced, with the condyle hopping over the posterior portion of the disc and recapturing the disc in its optimal relationship—centered on the head of the condyle. In ADD with reduction, there typically are two pops or clicks that occur—the first occurring during opening (the reduction of the disc), followed by the second pop or click as the posterior teeth are coming into terminal contact (the displacement of the disc). ADD and the corresponding misalignment of the TMJs creates unwanted torque in the upper cervical spine due to nociceptive signaling. This creates reflex contraction of the upper cervical muscles (especially the subocciptial muscle around C1/C2), leading to atlas and axis subluxation and head misalignment, and inducing neural shear.

After the patient is evaluated, TENS is applied to the patient's temporomandibular region (110) to stimulate cranial nerve V (the trigeminal nerve). Repetitive patterns of muscle contraction (like closing on our back teeth) develop muscle engrams, which are defined as an interneuronal circuit involving specific neurons and muscle fibers that can be coordinated to perform specific motor activity patterns. TENS is used to deprogram this engram pattern of muscle contraction (which patients develop in which they close on their back teeth) and to locate optimized physiologic rest (CM alignment). Additionally, TENS of cranial nerve V will relax the lateral pterygoid muscle that is attached to the articular disc in the TMJs. If the patient has ADD, TENS is used to reduce the affected TMJ(s). After the articular discs are reduced, then the effects of torque induced by the TMJs are eliminated via TENS. The CM optimization process can be performed, including one or more (e.g., five) cycles of protruding the jaw, holding it protruded for one or more TENS pulses (seven, for instance) and allowing the jaw to float back to rest without closing on the posterior teeth. Once ADD is eliminated, the optimized CC/CM orthopedic alignment can be achieved.

As noted above, the TENS and CM optimization process relaxes the jaw muscles and deprograms them, facilitating TMJ disc reduction (relieving C1/C2 torque) correcting yaw and allowing for pinpointing of physiologic rest of the lower jaw when the muscles that support it are in a state of rest. Typically, the patient closes his or her jaw in an engrammed path so that the back teeth are in contact with each other on both the right and left side, and the lower front teeth are behind the upper front teeth. Absent of TMJ disc reduction and muscle deprogramming achieved by TENS, the muscles will continue to function in their engram pattern, pulling the jaw up and back to the habitual CC/CM orthopedic alignment, rather than the optimized alignment.

While TENS is being applied, the patient relaxes and does not attempt to move his or her jaw. The patient instead allows the jaw to hang and relax, keeping lips and teeth apart. In this embodiment, the TENS used to identify physiologic rest of the mandible is Ultra Low Frequency (ULF) TENS that generates pulses at 0.76 HZ. Communication with the muscles of mastication is via stimulation of the trigeminal nerve. Once a clinical stimulation threshold is achieved, the muscles that regulate lower jaw position will contract with each TENS pulse, causing visible anterior-posterior and vertical movement of the mandible. The amplitude of the TENS pulses is adjusted so that a small amount of jaw movement is noticeable to the practitioner's touch when a finger is rested on the subject's lower jaw. Movement of the jaw should not be great enough to cause the teeth of the lower jaw to touch those of the upper jaw. Between the TENS pulses, the jaw muscles are not stimulated. Over time, the muscles will deprogram and begin to approach their optimal physiologic resting length, allowing the mandible to approach its optimal resting position relative to the maxilla.

If popping or clicking in the TMJs was identified during the evaluation, the TMJ(s) must be reduced to ensure that the disks in the TMJs are properly positioned between the condyle and fossa in each joint (115). The reduction of the TMJs (if necessary) is performed while TENS is being applied. Visual examination is also performed during application of TENS to assess the orthopedic alignment as the patient presents from the frontal and lateral views, noting any CC/CM subluxation and its effect on head position and baseline balance point.

While TENS is being applied to the patient's temporomandibular region, the movement of the jaw is tracked (120). The jaw movement may be tracked in a number of ways. In one embodiment, an electronic tracking system such as the K7 Evaluation System by Myotronics, Inc. can be used as a means to objectively verify the subjective interpretation of the practitioner. More specifically, the tracking system can monitor the lower jaw's physiologic position when the muscles that support the lower jaw are at rest, and verify the trajectory the jaw will follow upon closing. In this embodiment, a magnet is secured to the patient's lower jaw prior to applying TENS. As TENS is applied, the position of the magnet is sensed by the electronic tracking system, providing an indication of the position of the lower jaw. The electronic tracking system may display the tracked position so that the practitioner can see an objective measure of the involuntary movement of the jaw resulting from TENS and compare that to the habitual (voluntary) movement of the jaw when the subject closes on his or her back teeth. Commonly, the jaw position (or more specifically the position of the magnet) will be plotted so that the relative movement of the magnet (hence the jaw) can be seen as the jaw is involuntarily moved by TENS and/or voluntarily by the patient.

It is not necessary to employ an electronic tracking system to monitor the position of the jaw while TENS is being applied to identify the physiologic position of rest of the lower jaw. As stated above, the K7 data is used to objectively verify what the practitioner sees subjectively when the alignment of the TMJs and the CM alignment has been identified. True physiologic rest during TENS is that point at which (1) any ADD in the TMJ/s has been reduced, (2) CC alignment has been optimized via cervical distraction and correction of head position and (3) CM alignment has been optimized such that the muscles that support the lower jaw are at rest and not splinting against the TENS pulse. When these three conditions have been achieved, the quality of the TENS pulse exhibited by the movement of the lower jaw will be its sharpest at the set amplitude of TENS that achieved clinical threshold as described above.

This is because: (1) torque in the TMJs has been relieved by disc reduction in the affected joint(s), and its subsequent torque on the upper cervical spine due to hyperactive suboccipital muscles connected to C1/C2 has relieved neural shear in the upper cervical spine; (2) optimized CC alignment has relieved further neural shear, improving neural conduction and muscle function; and (3) the lower jaw has now moved to its most optimized frontal lateral and anterior/posterior (AP) position. TMJs are functioning optimally because joint dysfunction has been corrected and the lower jaw is in its orthopedically optimized position of rest relative to the cranium. In one embodiment, a skilled practitioner watches the patient and tracks all of these variables that directly affect the motion of the jaw through observation to verify that the optimized orthopedic alignment of the CC/CM alignment holds. Then, the fitting and capturing of the jaw relationship can move forward to lock in the alignment for optimized orthopedic correction.

As the jaw relationship is optimized in this embodiment, the practitioner identifies physiologic rest of the jaw and verifies that the TMJ discs are recaptured (if ADD is identified upon examination). The practitioner also verifies that the TMJs are not allowed to displace, and that the CC and CM alignment holds as the lower jaw maintains it position of physiologic rest while TENS is applied. A practitioner may, for example, observe the CC alignment of the patient from the front to verify there is no side bending or rotation of the head complex or shoulder drop off. FIG. 7A illustrates an aligned position of the head, while FIG. 7B illustrates a non-aligned, side-bent position. The practitioner may also make a lateral observation to verify that there is no posterior-cranial rotation and that the ala-tragus line is level with the horizon. FIG. 8 illustrates an aligned position as observed laterally. Then, the practitioner makes a frontal observation of the mandible relative to the maxilla to ensure that the frontal/lateral position of the lower jaw at rest is correct in both conditions of single joint ADD, right/left (R/L) joint ADD or no joint ADD. Finally, after the two previous conditions are met, then the AP and vertical position of the lower jaw relative to the upper jaw is determined in its optimized TMJ/CC/CM relationship. While this does not provide an exact measurement of the jaw's motion, the process of TENS deprograming, TMJ management, CC alignment, then CM alignment provides for an optimally aligned TMJ/CC/CM complex, allowing the lower jaw to move to its most anterior/frontal-lateral/vertical position and promoting a greater physiologic change on the alignment of the postural chain.

The purpose of applying TENS is to relax the jaw muscles, to reduce displaced discs in cases of single or bilateral ADD of the TMJs, and to allow the jaw to achieve a deprogrammed physiological rest position, rather than to determine an objective measurement of the jaw's motion in arriving at this position. A skilled practitioner may actually be able to more accurately discern meaningful changes in the TMJ/CC/CM orthopedic position because the electronic tracking system provides objective measurements of the lower jaw relative to the upper jaw and TMJs, but does not, in and of itself, provide any context for this complex of information. In other words, the data from the electronic tracking system could indicate proper alignment of the patient's bite while the patient has a visibly obvious misalignment of the CC/CM complex. In another alternative embodiment, both subjective observation of the patient and electronic systems may be used to track the movement of the patient's jaw as TENS is applied (or one may be used to verify the other).

While TENS is being applied to the patient's jaw, the practitioner carefully orthopedically aligns the CC complex of the patient's head and neck with the spine (125). Since it is common for a person's natural bite to be posterior to an optimized position (as shown in FIG. 2, for example), from a lateral view the person's head will typically be in a position that is forward from an orthopedically aligned position, exhibiting posterior-cranial rotation. Viewed from the frontal plane, it can also be side-bent or rotated as well, causing a cascade of misalignment down the postural chain all the way to the feet. For example, FIG. 9 illustrates the misalignment of the postural chain from the head to the hips that can result from misalignment of the TMJ/CC/CM complex.

When the patient's posture is laterally viewed, forward head position will present itself clinically by viewing three distinct postural relationships. First, the anterior-most portion of the maxilla is inspected to determine whether it is anterior to the sternum of the chest. Second, it is determined whether the patient's ears are forward somewhat from a position that is directly above the center of the shoulders. Third, the patient's ala-tragus line is inspected to evaluate for posterior-cranial rotation. Normally, the head should be oriented so that the Ala-Tragus line (the imaginary line that extends from the inferior border of the ala of the nose to the superior border of the triages of the ear) is level with horizon. If the ala is superior to the tragus when visualizing the ala-tragus line, then the head is tilted or pitched up, leading to subluxation of the atlas (C1).

Similarly, the frontal plane is examined in the following there ways. First, the pupillary line (an imaginary line connecting the patient's pupils) should normally be level when the head and upper cervical spine are in orthopedic alignment. However, if one pupil is positioned higher than the other, then the head is side-bending away from the higher pupil. Second, the facial midline (a reference line obtained by joining two points of the face—the glabella, which is the midpoint between the eyebrows, and the subnasale, which is the base of the nose) can be used to detect side bending of the head. Normally, this line would be perpendicular to horizon. Third, zygoma cheek display should appear equal in display from a frontal view if no head rotation is present. If the display does not appear equal, the head is rotated towards the less prominent zygoma cheek display. It will be necessary to correct these CC misalignments before proceeding on to capturing the optimized CM jaw relationship. While TENS is applied first, lateral corrections are done via cervical distractions until within norms, then frontal alignment is corrected by eliminating any side bending or rotation until within norms to optimize the CC alignment.

By placing the patient's head in an orthopedically aligned CC position, subluxation of C1 and C2 is relieved. This reduces tension on the CM complex that would otherwise hold the jaw in a more posterior position and make it incapable of achieving its optimized position of rest. Additionally, eliminating subluxation of C1 and C2 reduces neural shear on the brainstem as described above, improving the range of motion of major joints. The practitioner can then make any necessary corrections to the alignment of the CM complex (130). As noted above, application of TENS to an amplitude that achieves clinical threshold will cause the patient's jaw muscles to contract, causing the jaw to elevate approximately 1-2 mm in a vertical and anterior-posterior trajectory. In a typical case, both of these improvements in C1/C2 alignment and relief of neural shear can be confirmed while correcting CC alignment. During cervical distraction to correct lateral alignment to within norms, the force of muscle contractions will increase without any change in TENS amplitude. This is a sign that relief of neural shear has improved neural conduction, and that the improved CC alignment has placed the CM relationship into an optimized physiology output zone. This and the alignment of the CM complex allows for more efficient motor recruitment and more forceful muscle contractions. The practitioner will be able to use this as a means to verify optimal orthopedic alignment of the head and upper cervical spine and move on to the frontal corrections.

With the CC/CM complex of the patient orthopedically aligned, deprogramming of the jaw muscles through application of TENS will cause the lower jaw to move toward an orthopedically optimized physiological rest position anterior to that achieved by TENS alone. This orthopedically optimized rest position will normally be different from a physiological rest position that is determined without the step of aligning the patient's head and upper cervical spine. Since the habitual bite position of the patient typically will have been posterior to the desired orthopedically optimized position (the habitual bite position corresponding to the upper and lower molars and premolars being in contact with each other and the lower front teeth posterior to the upper front teeth as shown in FIG. 2), this process typically involves a down and forward movement of the lower jaw to regain AP and posterior vertical space as well as correcting any pitch/yaw/roll imbalances in the habitual jaw relationship. As the jaw moves closer to an orthopedically optimized rest position (as illustrated in FIG. 3), the forward movement becomes more gradual and simple application of TENS (with orthopedic alignment of the head and neck) may not be sufficient to achieve a fully optimized rest position of the lower jaw. The process of achieving the orthopedically optimized physiological rest position may be more rapidly effectuated (and is necessary in cases of ADD to reduce TMJ discs to relieve torque in the CC complex) by having the patient extend his or her lower jaw forward as far as possible for some period of time (e.g., 7 seconds) and relaxing the jaw, which allows it to move backward toward the optimized rest position. Repeating this several times will normally result in a rest position of the lower jaw which is slightly forward of the position that would be achieved by applying TENS without forward extension of the jaw. This more forward rest position is typically closer to the desired orthopedically optimized rest position.

As noted above, the motion and position of the jaw can be tracked visually or using an automated electronic tracking system, or both, to verify that the deprogramming of the jaw has been successful and that the jaw assumes an orthopedically optimized rest position. At this point, the practitioner can take a bite registration to record the relative positions of the upper and lower jaws (135). The bite registration is taken using conventional means. Typically a Polyvinylsiloxane heavy body impression material is injected into the patient's mouth (onto the bite surfaces of the lower teeth, for example), and the patient is instructed to allow the jaw to float back to the desired optimized position of rest. Since the jaw muscles have been deprogrammed and the patient's head and neck are in an orthopedically aligned position, the patient's jaw should close to a position that is optimized to maintain the orthopedic alignment of the head and upper cervical spine. In this position, the articular disks in the TMJs will be reduced correcting the frontal-lateral (yaw) deviations, while the condyles will generally be centered in the fossa and stable, without producing any ADD upon closing into the bite registration. With TENS turned off, the practitioner may verify that the articular disks are reduced. If the disks are not reduced, the mandible is not in an orthopedically optimized position, so the procedure of FIG. 1 should be repeated. If, on the other hand, it is verified that the articular disks are reduced, the recorded bite registration should represent an orthopedically optimized position of the CC/CM complex. Preferably, a vertical index of 17-21 mm will be developed in the optimized jaw relationship (or in some situations, a minimum of 2 mm of space) between the closest approximation of teeth (the closest the upper and lower teeth come to touching each other) in the optimized jaw relationship.

In one embodiment, the bite registration may be taken (at least partially) by applying TENS to the patient's jaw muscles. As noted above, applying TENS to these muscles will cause the jaw to move, opening and closing slightly. If the bite registration material is placed on the patient's teeth and TENS is applied, the jaw will continue to move, slightly opening and closing, and not being inhibited from moving by the bite registration material. The amplitude of the TENS pulses is to be adjusted to a "clinical threshold", causing the jaw to elevate 1-2 mm each time the TENS stimulates the muscles of mastication to contract. As a result, the jaw closes enough to make at least a slight impression of the teeth in the bite registration material at the desired vertical index, or at least within 2 mm of the closest approximation of teeth in the optimized jaw relationship. The jaw may be closed on the bite registration material by having the practitioner instruct the patient to gently bite down on the material, or the amplitude of the TENS pulses may be increased to cause the patient's jaw to close with increasing force.

After the bite registration has been taken, the practitioner may verify that the bite properly records the orthopedically optimized position of the jaw. As discussed above, the tracking may be performed visually by the practitioner, it may be performed using an electronic tracking system, or a combination of these tracking techniques may be employed.

Additionally, the patient's range of motion of major joints, balance and center of gravity, or other aspects of his or her performance limitations or physiologic limitations can be evaluated to determine whether the jaw position recorded by the bite registration improves the patient's performance. If it appears during physiologic testing that the bite registration does not record the optimized jaw position, one or more additional bite registrations can be taken. The bite registration that is determined to record the most optimized jaw position via physiologic testing can then be selected for use in making an OAD.

In order to make the OAD, impressions of the patient's teeth should be taken. The impressions are negative molds of the patient's upper and lower teeth. Preferably, the impressions include all of the patient's teeth, although this may not be necessary in all cases. The making of the impressions involves conventional techniques in which, for example, impression material is mixed and placed in mold trays, which are then placed in the patient's mouth so that the impression material surrounds and contacts the surfaces of all of the teeth. Impressions of the upper teeth and the lower teeth are commonly made separately. When the impression material sets, the trays and the material are removed from the patient's mouth and are allowed inspected to ensure that the impressions are satisfactory. If the impressions are satisfactory, the impression material is allowed to fully cure and degas before material is poured into the impressions to make models of the teeth.

When the impressions have been completed, they are used to form positive molds of the patient's upper and lower teeth. Again, conventional techniques are used to make the positive molds. The molds are essentially plaster replicas of the patient's upper and lower teeth. These positive molds are mounted on an articulator. The articulator is a hinged device that allows the molds to move in a manner similar to the movement of the patient's jaw. The bite registration is used to align the positive molds so that the orthopedically optimized bite position recorded by the bite registration is replicated by the molds and articulator. This is accomplished by placing the mold of the upper teeth in the corresponding indentations on the upper side of the bite registration, and placing the mold of the lower teeth in the corresponding indentations on the lower side of the bite registration.

With the positive molds of the patient's teeth mounted on the articulator and aligned with the bite registration, an OAD can be formed between the upper and lower molds. The articulator is fixed in a position corresponding to the bite registration in which the upper and lower front teeth preferably are not touching, and posterior support of the upper and lower molars and premolars on both the right and left side are preferably simultaneously engaging, not allowing the jaw to pitch up on either side. Posterior vertical support will be sufficient to allow for a vertical index of 17-21 mm or a minimum of 2 millimeters apart at the closest approximation of the teeth.

The OAD can be made from any suitable material, such as double-layered heat- and pressure-laminated EVA type material. The selected material may be formed in accordance with the manufacturer's recommendations and requirements for the material. In the final OAD, the material will fill the space between the upper and lower molars and premolars. In one embodiment, the OAD does not have any material that is positioned between the upper and lower incisors and canines. In this embodiment, a piece of connecting material extends between left and right portions of the OAD behind the lower front teeth. This structure may be obtained by forming the OAD material between the molds of the upper and lower teeth, and then removing the material between the incisor and canine teeth. Alternatively, the OAD can be formed by initially positioning the material only between the upper and lower molars and pre-molars, and not between the upper and lower incisors and canines. In either case, the OAD may have to be trimmed to remove unwanted material, remove sharp edges, or otherwise refine the final shape of the OAD.

Figure 4:
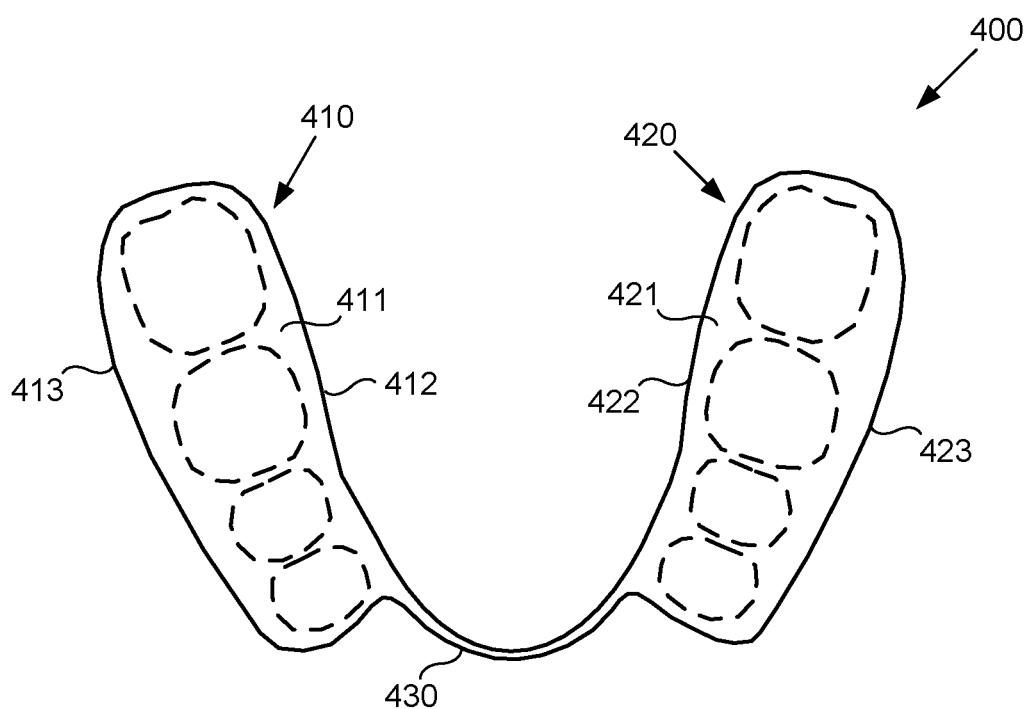
FIG. 4 is a diagram illustrating a top view of an OAD in accordance with one embodiment.
Figure 5:
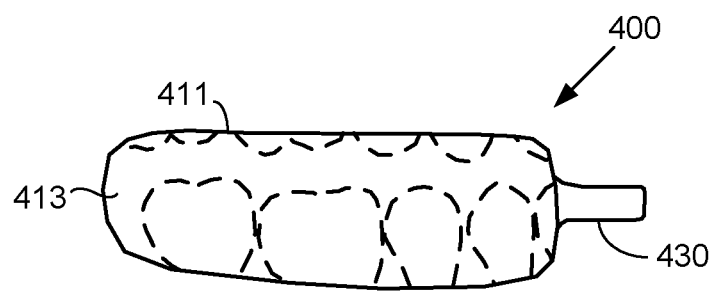
FIG. 5 is a diagram illustrating a side view of an OAD in accordance with one embodiment.

Referring to FIGS. 4 and 5, an exemplary OAD formed by the present methods is shown. In this embodiment, OAD 400 includes two bite portions 410 and 420. OAD 400 is shown from the top in this figure, so bite portion 410 fits between the upper and lower molars and pre-molars on the right side of the patient's mouth, and bite portion 420 fits between the upper and lower molars and pre-molars on the left side of the patient's mouth. Each of bite portions 410 and 420 has a bite surface (411, 421) that is positioned between the respective upper and lower teeth. Each of the bite portions also has an inner wall (412, 422) and an outer wall (413, 423) that extends downward form the bite surface (411, 412) to cover the lower teeth. The inner and outer walls of the bite portions, as well as the lower bite surfaces, are molded to the lower teeth so that OAD 400 is retained on the lower teeth. A connecting portion 430 extends from the front end of bite portion 410 to the front end of bite portion 420 so that the portions form a single unit.

Figure 6A:
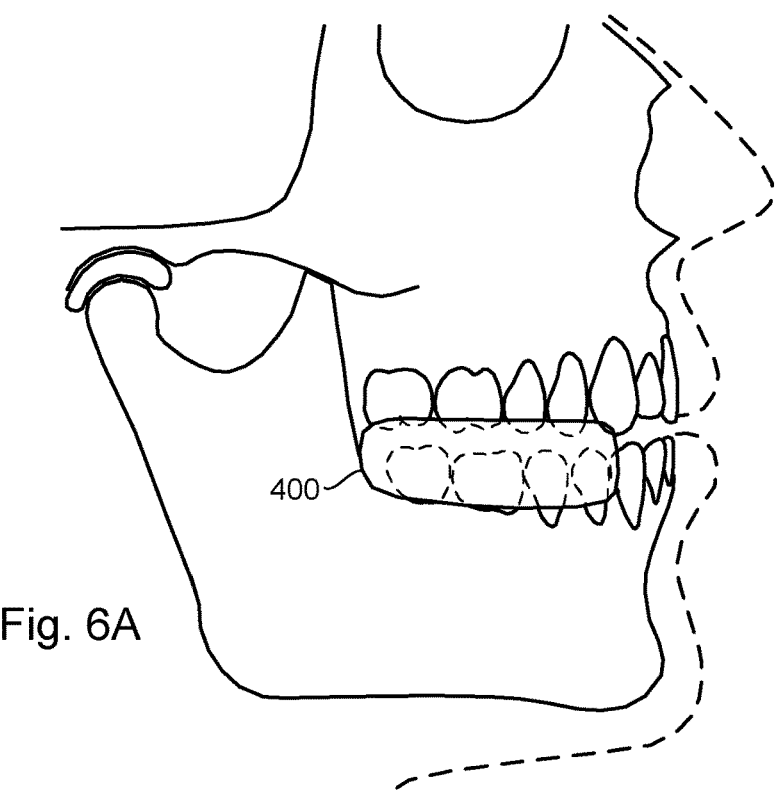
FIGS. 6A and 6B are diagrams illustrating a patient's jaw with an OAD positioned on the patient's lower teeth in accordance with one embodiment.
Figure 6B:
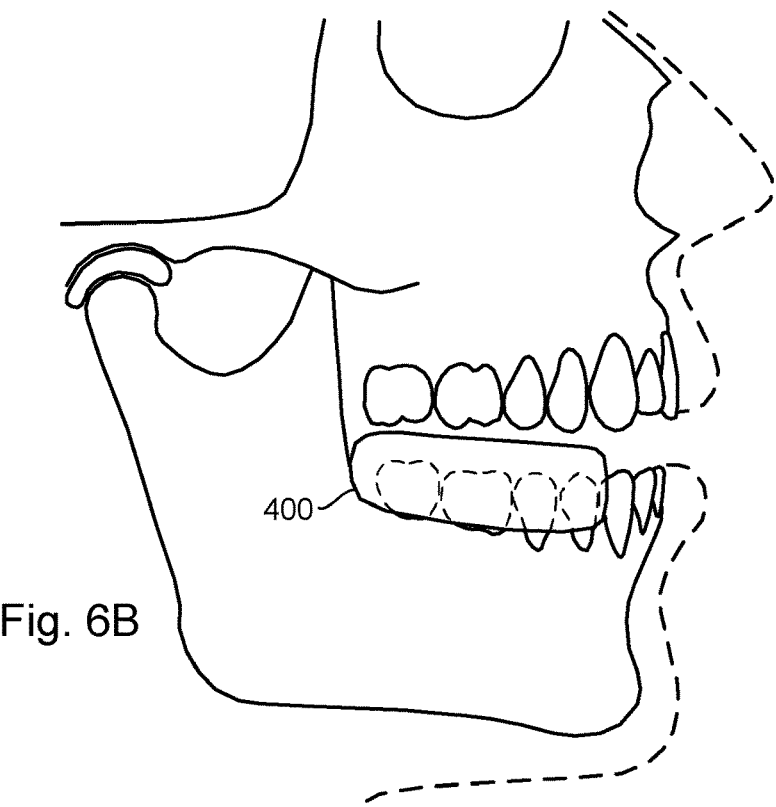

Referring to FIGS. 6A and 6B, a pair of diagrams are provided to illustrate the exemplary OAD of FIGS. 4 and 5 in position on a patient's lower teeth. As depicted in this figure, OAD 400 rests on the lower teeth and is molded to the lower teeth so that the OAD is retained on the lower teeth. When the patient's jaw is closed as shown in FIG. 6A, the patient's teeth fit within the indentations in the OAD, thereby holding the patient's lower jaw in the orthopedically optimized position discussed above. When the patient's jaw is open as shown in FIG. 6B, the OAD remains positioned on the patient's lower teeth.

When the patient opens his or her mouth as shown in FIG. 6B, the OAD remains in position on the lower teeth and does not impede speech or breathing. Additionally, because the OAD rests on the lower teeth, it does not fall out of position, as might be the case with an OAD that is retained on the upper teeth. As the patient's jaw is closed, the gap between the OAD and the patient's upper teeth is reduced. As noted above, the OAD is formed using the orthopedically optimized position of the jaw, so when the upper teeth contact the OAD, they fit into the indentations in the upper bite surfaces, drawing the lower jaw to the orthopedically optimized position. Further, because the jaw is in the orthopedically optimized position when bite pressure is encountered by the molars and pre-molars, the brain senses the position of the jaw (through proprioception) as the orthopedically optimized position. As noted above, the brain determines where to position the head and upper cervical spine based on the jaw position, so when it senses the jaw in the orthopedically optimized position, the brain determines that the head and upper cervical spine should be in orthopedic alignment, which is associated with the orthopedically optimized position.

It should be noted, however, that alternative embodiments of the present OAD may be retained on the upper teeth. As noted above, the use of the OAD and the resulting improvement of orthopedic alignment in the user's jaw and upper cervical spine reduces occlusion of the user's airway, which may in turn decrease the incidence of snoring or obstructive sleep apnea. The fact that the OAD does not impede breathing makes it even more useful as an aid to prevent snoring and sleep apnea.

Figure 10:
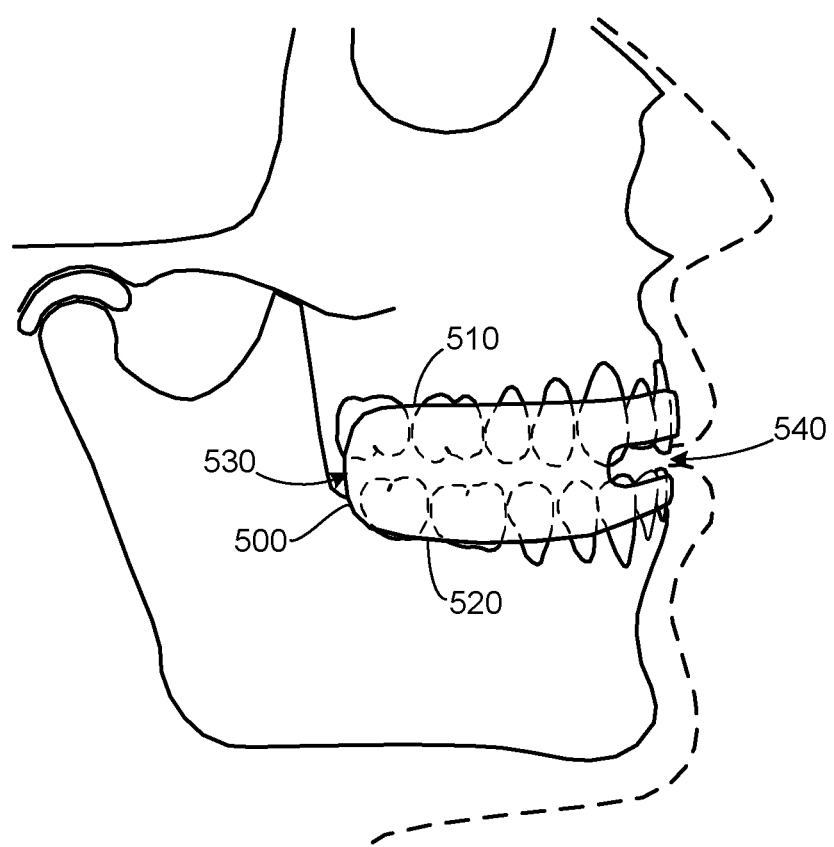
FIG. 10 is a diagram illustrating a patient's jaw with an OAD designed for use as a sleep aid to reduce snoring or obstructive sleep apnea.

While the embodiment of the OAD illustrated in FIGS. 4-6 is retained on the lower teeth, an alternative embodiment that is designed for use as a sleep aid to reduce snoring or obstructive sleep apnea covers both the lower and upper teeth. This embodiment is illustrated in FIG. 10. As shown in this figure, OAD 500 includes a portion 510 that fits over the upper teeth, a portion 520 that fits over the lower teeth, and a connecting portion 530 between the upper and lower portions. The use of portions that cover both the upper and lower teeth helps to retain the OAD in position in the patient's mouth. The OAD also helps to keep the patient's jaws together, rather than allowing gravity to pull the mandible and the lower teeth away from the upper teeth. In this embodiment, the upper and lower portions of the OAD each extend over the front teeth to help ensure that the OAD remains in position in the patient's mouth while the patient is lying down. Connecting portion 530 does not extend all the way to the front teeth. Instead, an opening 540 is provided between upper portion 510 and lower portion 520 at the front teeth so that the patient will be able to easily breathe when wearing the OAD.

It should be noted that there may be many variations of the foregoing embodiments that are within the scope of the claims below. For example, in one embodiment, a method may include applying TENS to a patient, orthopedically aligning the patient's head and neck, and taking a bite registration, while another embodiment may include evaluating and reducing the patient's TMJs, and yet another embodiment may include taking an orthopedically optimized bite registration for the patient and forming an OAD for the patient that holds the patient's jaw in an orthopedically optimized position. The various steps of the present methods need not be performed in a specific order, unless specifically noted otherwise. For instance, the application of TENS to the patient may be performed before, after, or concurrently with the orthopedic alignment of the patient's head and neck.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A method comprising:
    applying transcutaneous electric neural stimulation (TENS) to a patient's jaw muscles;
    orthopedically aligning at least the atlas and axis of the patient's upper cervical spine while applying TENS to the patient's jaw muscles, thereby minimizing neural shear and causing the patient's temporo-mandibular joints (TMJs) to move to an orthopedically optimized position; and
    while the atlas and axis of the patient's upper cervical spine are orthopedically aligned and neural shear in at least the atlas and axis of the patient's upper cervical spine is minimized, taking a bite registration of the upper and lower jaws.

2. The method of claim 1, wherein orthopedically aligning the atlas and axis of the patient's upper cervical spine comprises ensuring that the patient's bipupillary line is level with the horizon.

3. The method of claim 1, wherein orthopedically aligning the atlas and axis of the patient's upper cervical spine comprises ensuring that the patient's ala-tragus line is level with the horizon.

4. The method of claim 1, wherein orthopedically aligning the atlas and axis of the patient's upper cervical spine comprises ensuring that the patient's ears are aligned directly above the patient's shoulders, hips, knees and heels.

5. The method of claim 1, further comprising, prior to applying TENS to the patient's jaw muscles, reducing the patient's TMJs, thereby positioning an articular disk of each TMJ between a corresponding condyle of the patient's lower jaw and a corresponding glenoid fossa of the patient's skull.

6. The method of claim 1, wherein the bite registration is taken with the patient's lower teeth at least 2 millimeters from the patient's upper teeth.

7. The method of claim 6, wherein the bite registration is taken with a vertical index of 17-21 millimeters.

8. The method of claim 6, wherein the bite registration is taken while the patient's lower front teeth are not touching the patient's upper front teeth.

9. The method of claim 1, wherein applying TENS to the patient's jaw muscles causes the patient's jaw to move to a rest position, the method further comprising, prior to taking the bite registration, performing one or more cycles, wherein each cycle comprises: extending the patient's lower jaw forward from the rest position to an extended protrusive position; maintaining the extended protrusive position for one or more TENS pulses; and allowing the TMJs to reduce and allowing the lower jaw to relax to the orthopedically optimized position.

10. The method of claim 1, further comprising providing molds of the patient's upper and lower teeth, positioning the molds in the orthopedically optimized position using the bite registration, and forming an orthopedic alignment device (OAD) between the molds.

11. The method of claim 10, wherein the OAD is formed so that when the OAD is positioned in the patient's mouth and the patient's jaw is closed, bite pressure is applied to the patient's upper molars and premolars and lower molars and premolars while the TMJs are in the orthopedically optimized position.

12. The method of claim 11, wherein the OAD applies bite pressure to the patient's upper molars and premolars and lower molars and premolars before bite pressure is applied to non-molars.

13. An orthopedic alignment device (OAD) formed by a process comprising the steps of:
    applying transcutaneous electric neural stimulation (TENS) to a patient's jaw muscles;
    reducing any articular disc displacement (ADD) in the temporo-mandibular joints (TMJs);

orthopedically aligning at least the atlas and axis of the patient's upper cervical spine while applying TENS to the patient's jaw muscles, thereby minimizing neural shear and causing the patient's cranio-cervical (CC)/cranio-mandibular (CM) complex to move to an orthopedically optimized position;

while neural shear in at least the atlas and axis of the patients upper cervical spine is minimized, taking a bite registration of the upper and lower jaws;

providing molds of the patients upper and lower teeth;

positioning the molds in the orthopedically optimized position using the bite registration; and forming an OAD between the molds.

14. The OAD of claim 13, wherein orthopedically aligning at least the atlas and axis of the patients upper cervical spine comprises ensuring that the patient's bipupillary line is level, ensuring that the patient's tragus line is level, and ensuring that the patient's ears are aligned with the patients shoulders.

15. The OAD of claim 13, wherein the OAD is formed so that when the OAD is positioned in the patient's mouth and the patient's jaw is closed, bite pressure is applied to the patient's upper molars and premolars and lower molars and premolars while the TMJs are in the orthopedically optimized and reduced position.

16. The OAD of claim 15, wherein the OAD is configured to apply bite pressure to the patient's upper molars and premolars and lower molars and premolars before bite pressure is applied to non-molars when the OAD is positioned in the patient's mouth and the patient's jaw is closed onto the OAD, and wherein the OAD prevents upper and lower anterior teeth make contact with each other.

17. The OAD of claim 15, wherein the OAD has bite portions that conform to bite surfaces of a patient's molars and premolars.

18. The OAD of claim 15, wherein the OAD prevents bite pressure from being applied to the patient's front teeth before bite pressure is applied to the patient's molars and premolars.

* * * * *